US009692950B2

United States Patent
Chang et al.

(10) Patent No.: US 9,692,950 B2
(45) Date of Patent: Jun. 27, 2017

(54) DISPLAY METHOD FOR VIDEO CONFERENCING

(71) Applicant: MediaTek Inc., Hsin-Chu (TW)

(72) Inventors: Chih-Kai Chang, Taichung (TW); Tsu-Ming Liu, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 0 days.

(21) Appl. No.: 15/002,448

(22) Filed: Jan. 21, 2016

(65) Prior Publication Data

US 2016/0241811 A1     Aug. 18, 2016

Related U.S. Application Data

(60) Provisional application No. 62/116,710, filed on Feb. 16, 2015.

(51) Int. Cl.
H04N 7/14    (2006.01)
H04N 5/225   (2006.01)
(Continued)

(52) U.S. Cl.
CPC ....... *H04N 5/2252* (2013.01); *G01N 15/1434* (2013.01); *G01N 21/53* (2013.01); *G01N 21/55* (2013.01); *G06F 1/1626* (2013.01); *G06F 1/1686* (2013.01); *G06F 3/016* (2013.01); *G06F 3/0414* (2013.01); *G06F 3/0416* (2013.01);
(Continued)

(58) Field of Classification Search
CPC ...... H04N 5/2252; H04N 7/15; H04N 5/2253; H04N 5/2257; H04N 5/2254; H04N 7/14–7/157; G06F 3/016; G06F 3/16; G06F 3/0416; G06F 3/0414; G06F 3/0484; G06F 3/0488; G06F 2203/04808; G06F 2203/04806; G06K 9/00255; G06T 7/0081; G06T 3/60; G06T 7/0051; G06T 2207/20144; G01N 21/55; G01N 15/1434;
(Continued)

(56) References Cited

U.S. PATENT DOCUMENTS 6,633,608 B1 *   10/2003   Miller ................. H04N 19/423
                                                              348/E5.104
2012/0229589 A1 *  9/2012  Barrus ................. H04N 7/147
                                                              348/14.08
(Continued)

*Primary Examiner* — Stella Woo
(74) *Attorney, Agent, or Firm* — McClure, Qualey & Rodack, LLP

(57) ABSTRACT

A display method for video conferencing and an associated video conferencing system are provided. The video conferencing system includes a display, an image capturing unit, and a network interface unit. The method includes the steps of: utilizing the image capturing unit to capture images of a local user in a video conference; performing foreground segmentation on the captured images to obtain a foreground object; flipping the foreground object horizontally; identifying a human face from the flipped foreground object and correcting a facing angle of the human face; determining interaction data from the local user on the display; encoding the interaction data and the flipped foreground object into an interaction stream and a video stream, respectively; packing the interaction stream and the video stream into an output stream; and transmitting the output stream to a remote user of the video conference through the network interface unit.

20 Claims, 9 Drawing Sheets

(51) Int. Cl.
- *G06F 3/0488* (2013.01)
- *G06K 9/00* (2006.01)
- *G06T 3/60* (2006.01)
- *H04N 7/15* (2006.01)
- *G01N 15/14* (2006.01)
- *G01N 21/53* (2006.01)
- *G01N 21/55* (2014.01)
- *G06F 3/041* (2006.01)
- *G06F 3/0484* (2013.01)
- *G06F 3/16* (2006.01)
- *G06F 3/01* (2006.01)
- *G06F 1/16* (2006.01)
- *H04M 1/02* (2006.01)

(52) U.S. Cl.
CPC .......... *G06F 3/0484* (2013.01); *G06F 3/0488* (2013.01); *G06F 3/16* (2013.01); *G06K 9/00255* (2013.01); *G06T 3/60* (2013.01); *H04M 1/0264* (2013.01); *H04N 5/2253* (2013.01); *H04N 5/2254* (2013.01); *H04N 5/2257* (2013.01); *H04N 7/144* (2013.01); *H04N 7/15* (2013.01); *G01N 2201/062* (2013.01); *G01N 2201/0638* (2013.01); *G06F 2203/04806* (2013.01); *G06F 2203/04808* (2013.01); *H04N 2007/145* (2013.01)

(58) Field of Classification Search
CPC .......... G01N 21/53; G01N 2201/0638; G01N 2201/062
See application file for complete search history.

(56) References Cited

U.S. PATENT DOCUMENTS

| | | | |
|---|---|---|---|
| 2013/0093838 A1* | 4/2013 | Tan | H04N 7/144 348/14.16 |
| 2014/0347436 A1* | 11/2014 | DeMerchant | H04N 7/142 348/14.08 |
| 2015/0009277 A1* | 1/2015 | Kuster | G06T 15/205 348/14.07 |
| 2015/0244976 A1* | 8/2015 | Chen | H04N 7/141 348/14.07 |
| 2015/0334398 A1* | 11/2015 | Socek | H04N 19/146 375/240.26 |

* cited by examiner

DISPLAY METHOD FOR VIDEO CONFERENCING

CROSS REFERENCE TO RELATED APPLICATIONS

This application claims the benefit of U.S. Provisional Application No. 62/116,710 filed on Feb. 16, 2015, the entirety of which is incorporated by reference herein.

BACKGROUND OF THE INVENTION

Field of the Invention

The present invention relates to video conferencing, and, in particular, to a display method for video conferencing and an associated video conferencing system.

Description of the Related Art

In recent years, video conferencing has become important way for two remote users to communicate, thanks to the development of network technologies and video compression technologies. Generally, it is necessary for a user to own a dedicated video conferencing system to conveniently conduct video conferencing with other users. The video conferencing systems on the market are usually equipped with a camera, a microphone, and a controller. However, a conventional video conferencing system can only be used to conduct a video conference, and the users in the video conference are not able to interact with each other by writing or drawing something on their displays, resulting in a poor user experience and insufficient immersion sense.

Accordingly, there is a demand for a display method for video conferencing and an associated video conferencing system to solve the aforementioned problems.

BRIEF SUMMARY OF THE INVENTION

A detailed description is given in the following embodiments with reference to the accompanying drawings.

In an exemplary embodiment, a video conferencing system is provided. The video conferencing system comprises: a display; an image capturing unit comprising an image sensor to capture images of a local user in a video conference; a network interface unit, configured to exchange output streams from the local user and a remote user in the video conference; and a processor, configured to perform foreground segmentation on the captured images to obtain a foreground object, and flip the foreground object horizontally. The processor further identifies a human face from the flipped foreground object and corrects a facing angle of the human face in the flipped foreground object toward the image capturing unit. The processor further determines interaction data from the local user on the display, and encodes the interaction data and the flipped foreground object with the corrected human face into an interaction stream and a video stream, respectively. The processor further packs the interaction stream and the video stream into the output stream, and transmits the output stream to the remote user through the network interface unit.

In another exemplary embodiment, a display method for video conferencing, for use in a video conferencing system, is provided. The video conferencing system comprises a display, an image capturing unit, and a network interface unit. The method includes the steps of: utilizing an image sensor of the image capturing unit to capture images of a local user in a video conference; performing foreground segmentation on the captured images to obtain a foreground object; flipping the foreground object horizontally; identifying a human face from the flipped foreground object and correcting a facing angle of the human face in the flipped foreground object toward the image capturing unit; determining interaction data from the local user on the display; encoding the interaction data and the flipped foreground object with the corrected human face into an interaction stream and a video stream; packing the interaction stream and the video stream into an output stream; and transmitting the output stream to a remote user of the video conference through the network interface unit.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
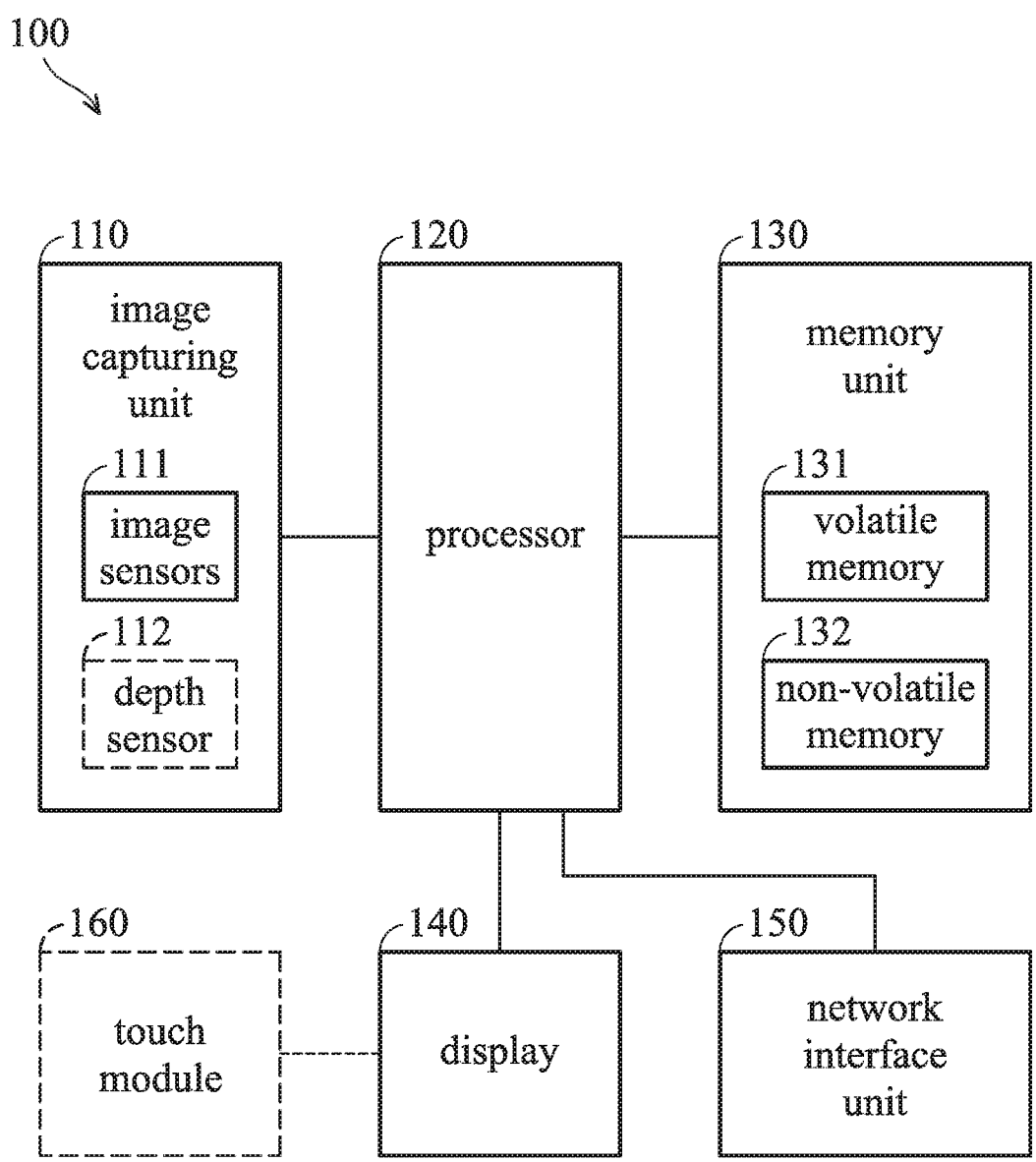
FIG. 1 is a block diagram of an video conferencing system 100 in accordance with an embodiment of the invention.

FIG. 1 is a block diagram of a video conferencing system 100 in accordance with an embodiment of the invention. As shown in FIG. 1, the video conferencing system 100 includes an image capturing unit 110, a processor 120, a memory unit 130, a display 140, and a network interface unit 150. The image capturing unit 110 is configured to capture images of a user. For example, the image capturing unit 110 comprises one or more image sensors 111 and a depth sensor, where the image sensors may be complementary metal-oxide-semiconductor (CMOS) sensors or charge-coupled device (CCD) sensors. In some embodiments, the image sensors 111 are arranged to capture stereoscopic images including a left-eye image and a right-eye image. In some embodiments, the image capturing unit 110 further comprises a depth sensor 112 that may be an infrared sensor including an infrared emitter and an infrared receiver (not shown).

The memory unit 130 may comprise a volatile memory 131 and a non-volatile memory 132. For example, the volatile memory 131 may be a static random access memory (SRAM), or a dynamic random access memory (DRAM), but the invention is not limited thereto. The non-volatile memory 132 may be a hard disk, a flash memory, etc. The non-volatile memory 132 stores a video conferencing program for processing the captured images of participants in a video conference, and processing interactions of the participants during the video conference. The processor 120 loads program codes of the video conferencing program stored in the non-volatile memory 132 into the volatile memory 131, and performs corresponding image processing on the images captured by the image capturing unit 110.

In some embodiments, the display 140 may be a liquid-crystal display (LCD), a light-emitting diode (LED) display, or an organic light-emitting diode (OLED) display, but the invention is not limited thereto. In some embodiments, the display 140 is a transparent display implemented by LCD, or OLED technologies. In some embodiments, the video conferencing system 100 further includes a touch module 160 that is integrated with the display 140, and the display 140 having a touch function can be regarded as a touch display. It should be noted that the display 140 can be a transparent touch display by using the aforementioned technologies well-known to those skilled in the art, and thus the details will be omitted here. The network interface unit 150 is configured to exchange output streams from the local user and a remote user in the video conference using network packets.

Figure 2:
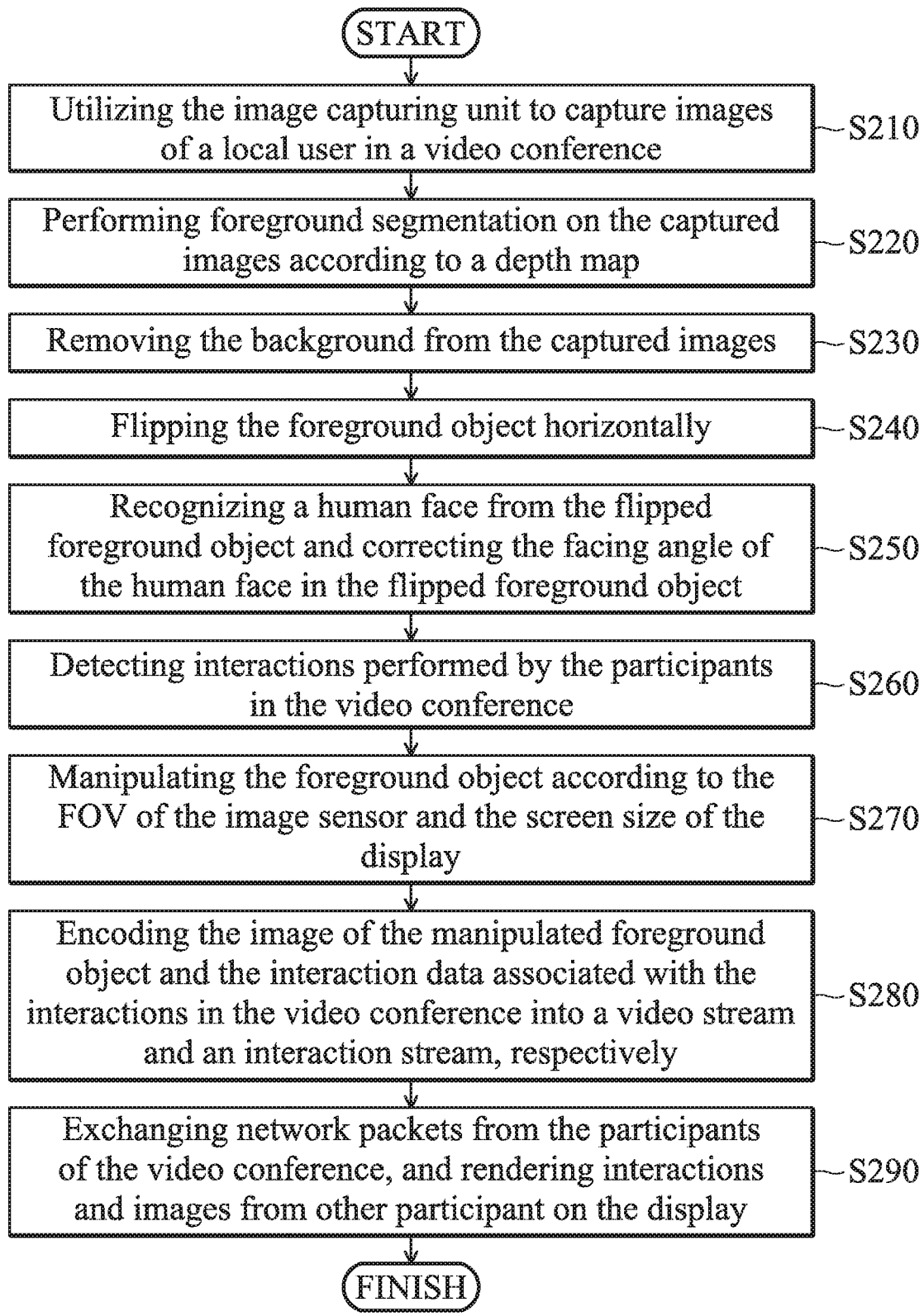
FIG. 2 is a flow chart of a display method for video conferencing in accordance with an embodiment of the invention.

FIG. 2 is a flow chart of a display method for video conferencing in accordance with an embodiment of the invention. In step S210, the image capturing unit 110 is utilized to capture images of a local user in a video conference. In step S220, foreground segmentation is performed on the captured images according to a depth map. For example, pixels of a foreground object in an image may have similar depth values that can be obtained by the depth sensor 112 of the image capturing unit 110 or by depth calculation using the captured images that can be stereoscopic images.

In step S230, the background is removed from the captured images. Thus, the processor 120 may perform subsequent image processing on the foreground object (e.g. the user). In step S240, the foreground object is flipped horizontally (i.e. right and left are reversed). It should be noted that step S240 can be omitted in some embodiments. In step S250, the human face is recognized from the flipped foreground object and the facing angle of the human face in the flipped foreground object is corrected as if the human face is looking toward the image capturing unit 110. For example, the image capturing unit 110 may be disposed at the corner, upper side, or the bottom side of the display 140. However, the user is usually facing toward the display 140 during the video conference, and that is the user does not actually face toward the image capturing unit 110, resulting in a slight difference of facing angles. Accordingly, step S250 is performed to correct the facing angle of the human face of the user.

In step S260, interactions performed by the participants in the video conference are detected. For example, the participants (e.g. the caller and callee, or the local user and the remote user) may draw something or write characters on the display 140, and the processor 120 may determine the interactions on the display 140. In step S270, the foreground object is manipulated according to the field of view of the image sensor 111 and the screen size of the display 140. For example, the field of view (FOV) of the image sensor 111 may be not adjusted to the most appropriate FOV during the video conference, and that is the foreground object may be oversized or undersized. The processor 120 may manipulate (e.g. resize or crop) the foreground object according to the FOV of the image sensor 111 and the screen size of the display 140, so that the manipulated foreground object may best fit the display 140.

In step S280, the image of the manipulated foreground object and the interaction data associated with the interactions in the video conference are encoded into a video stream and an interaction stream, respectively. The video stream and the interaction stream are packed up with timing information into an output stream. In step S290, the network packets from the participants of the video conference are exchanged, and the interactions and images from other participant can be rendered on the display 140 after the processor 120 has unpacked the output stream and decoded the video stream and interaction stream.

Figure 3:
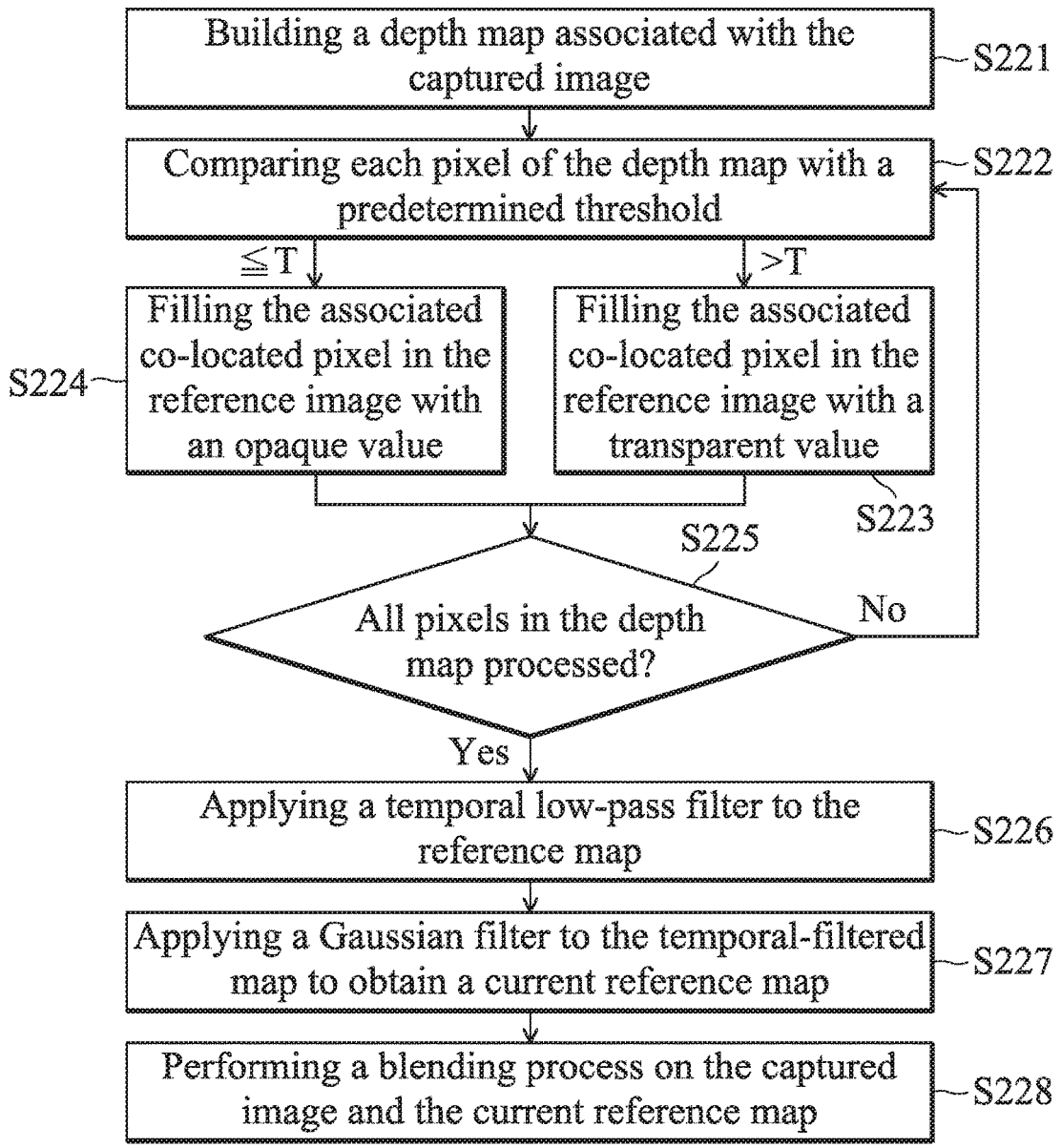
FIG. 3 is a flow chart of step S220 in the display method of FIG. 2.

FIG. 3 is a flow chart of step S220 in the display method of FIG. 2. Details of step S220 in the display method of FIG. 2 are further described. In step S221, a depth map associated with the captured image is built. For example, the depth map can be a gray-level image and each pixel in the depth map has an 8-bit or 16-bit value (not limited). The depth map can be obtained by using the depth information from the depth sensor 112 or by depth calculation using the captured images (e.g. stereoscopic images). In step S222, each pixel of the depth map is compared with a predetermined threshold. If the pixel value is larger than the predetermined threshold (e.g. background), the associated co-located pixel in a reference image is filled with a transparent value (e.g. $\alpha=0$) (step S223); and if the pixel value is smaller than or equal to the predetermined threshold (e.g. foreground), the associated co-located pixel in the reference image is filled with an opaque value (e.g. $\alpha=1$) (step S224). Accordingly, after processing each pixel in the depth map in step S222, a reference map can be obtained, where each pixel in the reference map represents the transparent value of the associated co-located pixel in the captured image. For example, each pixel in the reference map may be 0 or 1 to represent the transparency. In step S225, it is determined whether all pixels in the depth map have been compared with the predetermined threshold. If so, the flow proceeds to step S226. Otherwise, the flow goes back to step S222.

In step S226, a temporal low pass filter is applied to the reference map. For example, the reference maps of several previous images are stored in the memory unit 130, and thus the processor 120 may apply a temporal low pass filter to the reference maps of the current image and previous images to obtain a temporal-filtered reference map. It should be noted that the pixel values in the temporal-filtered reference map may be a floating-point number between 0 and 1. In step S227, a Gaussian spatial filter is applied to the temporal-filtered reference map to obtain a current reference map. For example, a two-dimensional Gaussian matrix is applied to each pixel of the temporal-filtered reference map. It should also be noted that the pixel values in the current reference map may be floating-point numbers between 0 and 1.

In step S228, a blending process is performed on the captured image and the current reference map. For example, the processor 120 may multiply each pixel in the captured image with the corresponding co-located pixel in the current reference map, and obtain the resulting image including the blended foreground object. The multiplied result corresponding to a pixel may be a floating point number between 0 and 255 (when the depth map has 8-bit), where the larger the multiplied result is the brighter the corresponding pixel. In some embodiments, when the display 140 is a first type of the transparent display, the dark content on the screen is transparent and the bright content is opaque. Alternatively, in some embodiments, when the display 140 is a second type of the transparent display, the dark content on the screen is opaque, and the bright content is transparent. It should be noted that the purpose for the blending process is that the background tends to be transparent and the foreground tends to be opaque when using a transparent display. The aforementioned blending process can be expressed by the following equation:

$$\text{pixel\_result} = \text{pixel\_CRM} * \text{pixel\_image} + (1 - \text{pixel\_CRM}) * D$$

where pixel_result denotes the output pixel in the resulting image; pixel_CRM denotes the value of a specific pixel in the current reference map; pixel_image denotes the value of the co-located pixel in the captured image associated with the specific pixel in the current reference map; D denotes the display-type factor, where D=255 when the display 140 is the second type, and D=0 when the display is the first type.

Accordingly, the processor 120 may determine that the foreground is opaque no matter whether the transparent display 140 is the first type or the second type, so that the foreground can be shown on the display 140 and the user may see the background in the user's local space through the display 140.

Figure 4:
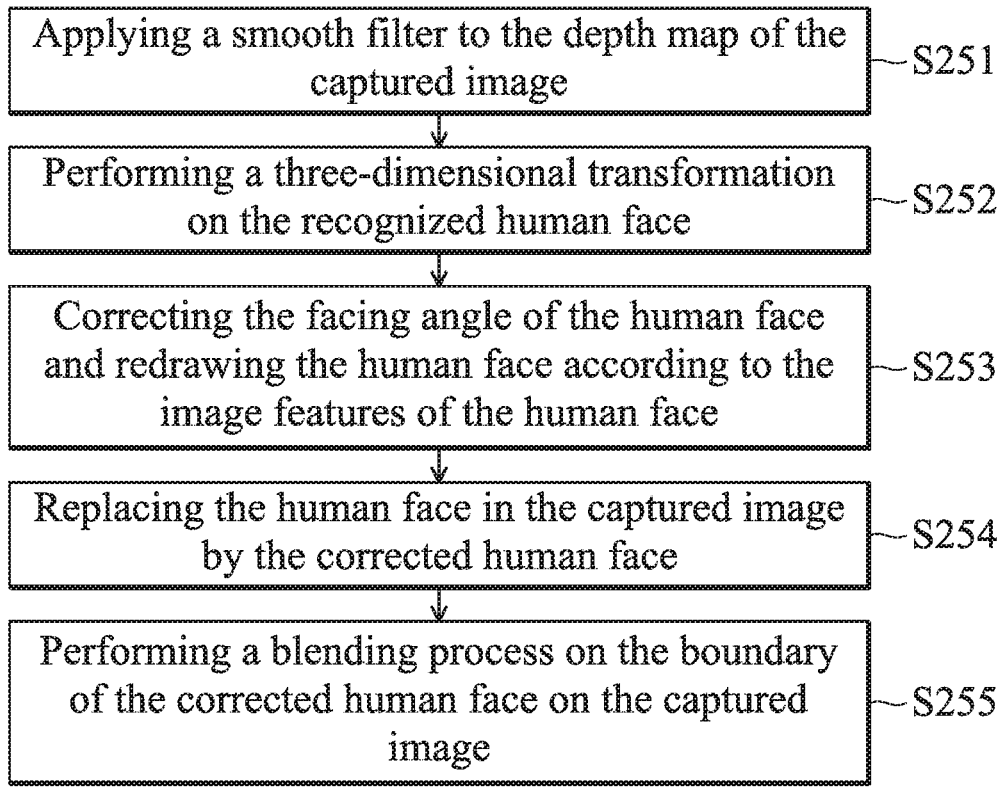
FIG. 4 is a flow chart of step S250 in the display method of FIG. 2.

FIG. 4 is a flow chart of step S250 in the display method of FIG. 2. In step S251, a smoothing filter is applied to the depth map of the captured image. It should be noted that the aforementioned depth map can be obtained from step S221 shown in FIG. 3. In step S252, a three-dimensional transformation is performed on the recognized human face. For example, the three-dimensional transformation is a shape-distorting transformation using projective mapping. In step S253, the facing angle of the human face is corrected (i.e. toward the image capturing unit 110) and redrawn according to the image features of the human face. For example, the image features may be eyes, nose, and mouth of the human face. In step S254, the human face in the captured image is replaced by the corrected human face. In step S255, a blending process is performed on the boundary of the corrected human face on the captured image, thereby reducing artifacts around the boundaries and edges of the correct human face. Accordingly, after performing the steps in FIG. 4, the other participant (i.e. remote participant) in the video conference may feel that the caller (i.e. local participant) is looking toward him.

Figure 5A:
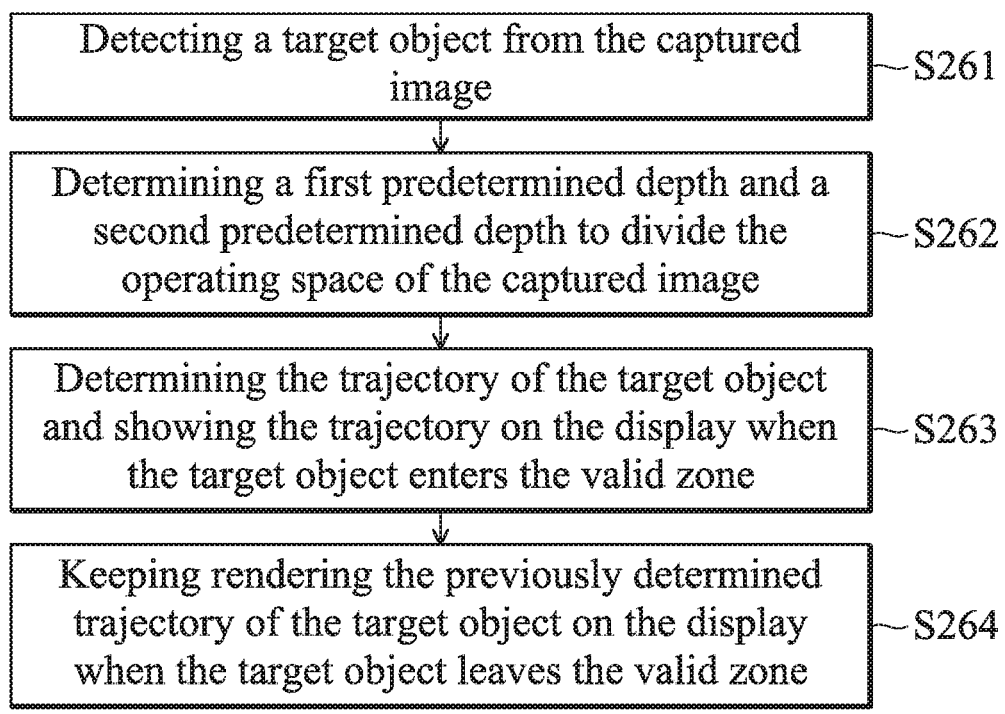
FIG. 5A is a flow chart of step S260 in the display method of FIG. 2.
Figure 5B:
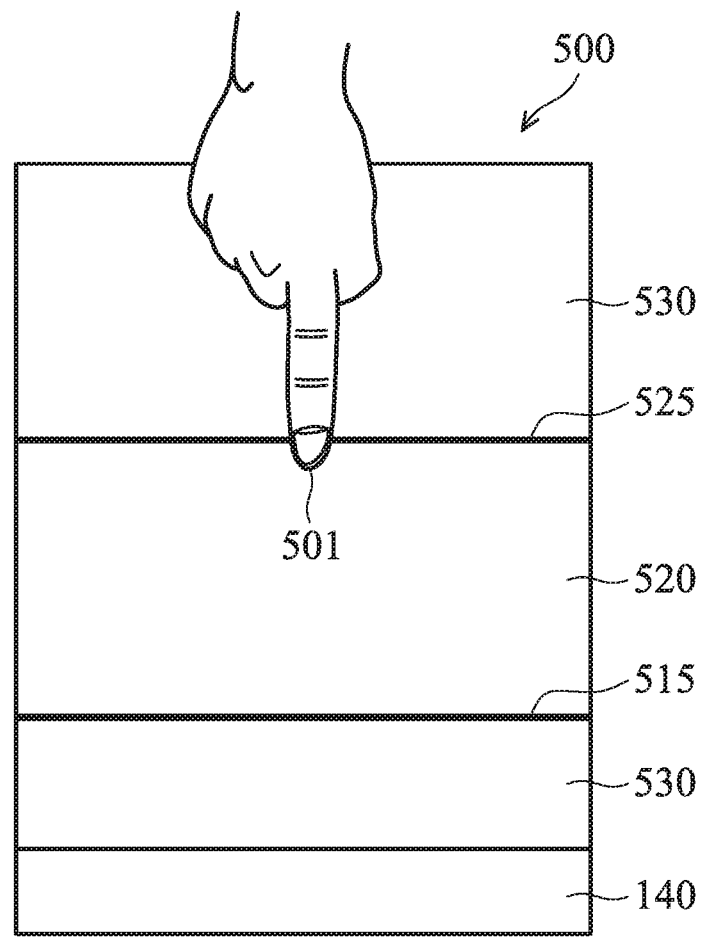
FIG. 5B is a diagram of the operating space of the captured image in accordance with an embodiment of the invention.

FIG. 5A is a flow chart of step S260 in the display method of FIG. 2. FIG. 5B is a diagram of the operating space of the captured image in accordance with an embodiment of the invention. Referring to both FIG. 5A and FIG. 5B, in step S261, a target object 501 is detected from the captured image. For example, the target object 501 may be a stylus or a fingertip of the user. It should be noted that techniques for detecting a stylus or a fingertip in an image are well-known to those skilled in the art, and thus the details will be omitted here. In step S262, a first predetermined depth and a second predetermined depth are determined to divide the operating space of the captured image. For example, the operating space 500 of the captured image can be divided into a valid zone 520 and an invalid zone 530, as shown in FIG. 5B. The valid zone 520 includes the space between a virtual plane 515 having a first predetermined depth and a virtual plane 525 having a second predetermined depth, where the second predetermined depth is larger than the first predetermined depth. The invalid zone 530 indicates the space other than the valid zone 520 (e.g. the space having a depth larger than the second predetermined depth or smaller than the first predetermined depth). Generally, the user is located in the invalid zone 530. When a target object (e.g. a hand of the user, a stylus, or a specific object) enters the valid zone 520, the user may perform interactions on the display 140 within the valid zone 520 via the target object.

In step S263, when the target object 501 enters the valid zone 520, the processor 120 may determine the trajectory of the target object and show the trajectory on the display 140. In step S264, when the target object leaves the valid zone 520, the previously determined trajectory of the target object is still kept rendering on the display 140. For example, the local participant of the video conference may want to write memos on the display 140, and share the memos with the remote participant. Specifically, the user may use his fingertip or a stylus to write something in the valid zone 520 or on the surface of the display 140, the processor 120 may record the trajectory of the fingertip or stylus, and keep rendering the previously recorded trajectory on the display 140 even if the fingertip or stylus has left the valid zone 520, so that the remote participant may see what the local participant has written on the display 140. It should be noted that the trajectory determination of the target object is image-based in the embodiment of FIG. 5A and FIG. 5B, and the display 140 may or may be not integrated with the touch module 160.

Figure 6:
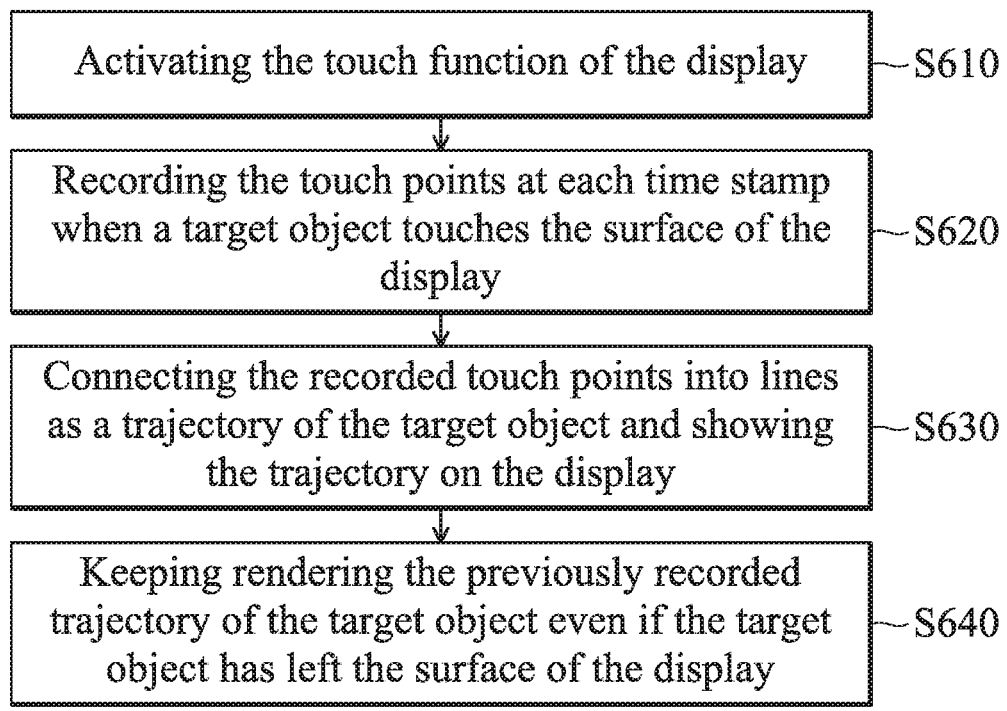
FIG. 6 is another flow chart of step S260 in the display method of FIG. 2.

FIG. 6 is another flow chart of step S260 in the display method of FIG. 2. In the embodiment of FIG. 6, the display 140 is integrated with the touch module 160, and thus display 140 is a touch display. In step S610, the touch function of the display 140 is activated. In step S620, when a target object (e.g. a fingertip or a stylus) touches the surface of the display 140, the touch points at each time stamp (e.g. per 1/30 second) are recorded by the processor 120. In step S630, the processor 120 connects the recorded touch points into lines as a trajectory of the target object, and shows the trajectory on the display 140. In step S640, the processor 120 keeps rendering the previously recorded trajectory of the target object even if the target object has left the surface of the display 140. It should be noted that the trajectory determination of the target object is touch-based in the embodiment of FIG. 6.

Figure 7A:
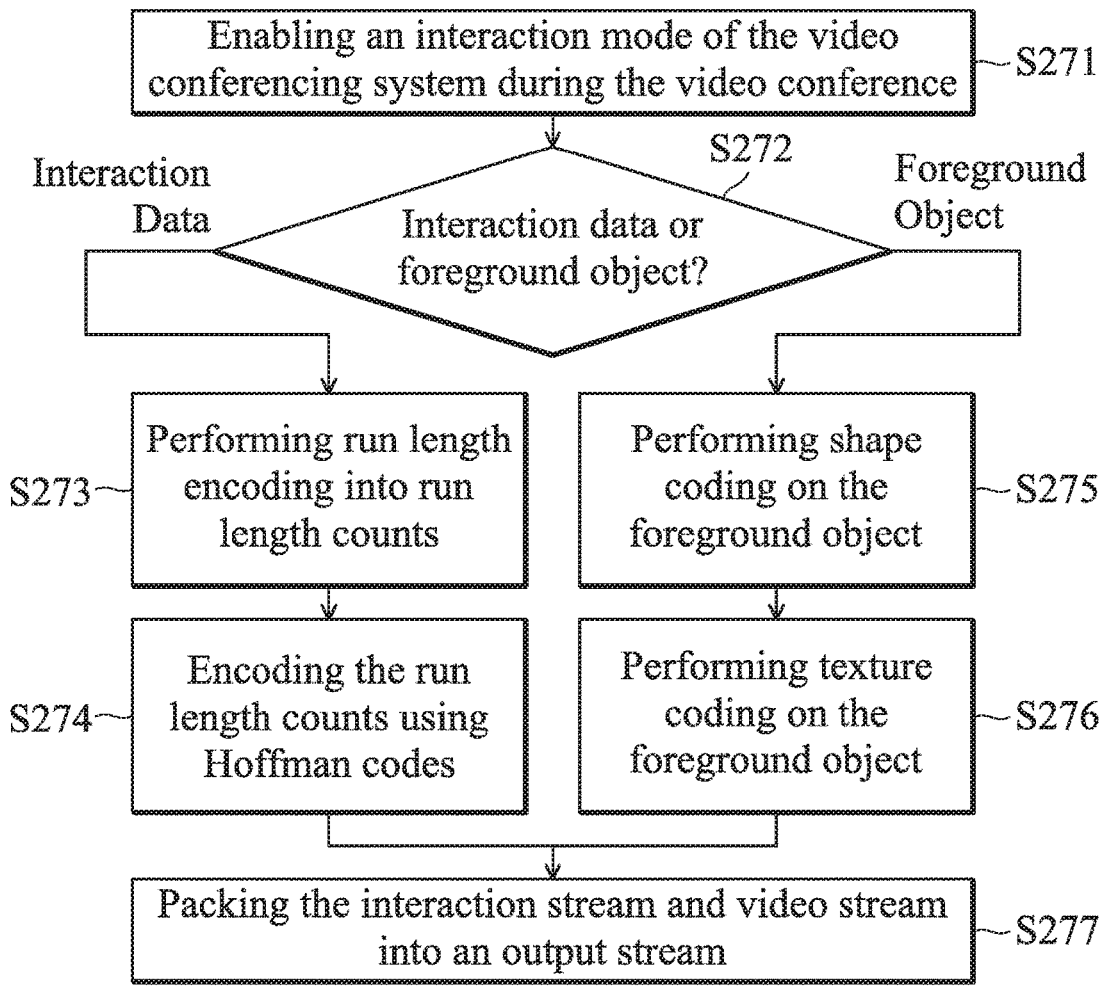
FIG. 7A is a flow chart of step S270 in the display method of FIG. 2.
Figure 7B:
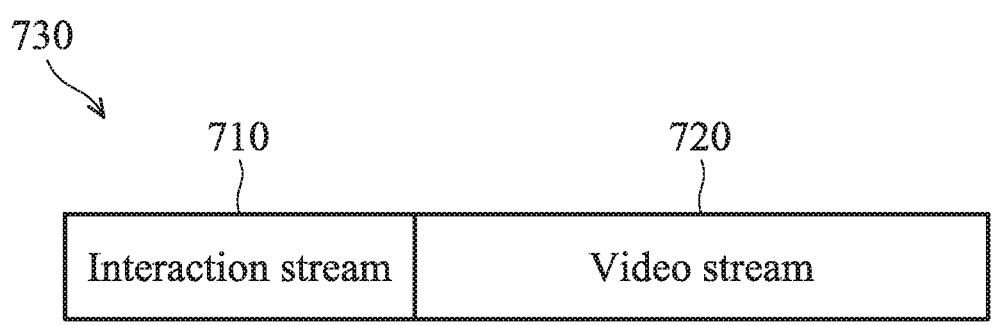
FIG. 7B is a diagram of the packed video stream with the foreground object and interaction data in accordance with an embodiment of the invention.

FIG. 7A is a flow chart of step S270 in the display method of FIG. 2. FIG. 7B is a diagram of the packed video stream with the foreground object and interaction data in accordance with an embodiment of the invention. Referring to FIG. 7A and FIG. 7B, in step S271, the user may enable an interaction mode of the video conferencing system 100 during the video conference. In step S272, it is determined whether the incoming data are interaction data or images of the foreground object. If the incoming data are interaction data, step S273 is performed. If the incoming data are images of the foreground object, step S275 is performed.

In step S273, run length encoding is performed on the interaction data into run length counts. In step S274, the run length counts are encoded using Hoffman codes. For example, the interaction data may record the trajectory of the user's touch actions on the display 140 or within the valid zone 520 (shown in FIG. 5B). The characteristics of the trajectory may be static and non-motion, and thus the trajectory can be represented by a binary image where 1 represents the pixel being touched and 0 represents the pixel being untouched. Accordingly, a simple intra-frame coding technique such as run length encoding using Hoffman codes can be used to encode the binary image recording the trajectory of interactions, and the size of interaction data can be significantly reduced when the interaction data is encoded into the interaction stream 710.

Due to the removal of the background, the foreground object can be regarded as a video object plane, and thus the foreground object can be encoded using MPEG4 inter-frame video-object-plane-based coding techniques. For example, in step S275, shape coding is performed on the foreground object, and then texture coding is performed on the foreground object (step S276) to generate a video stream 720.

In step S277, the interaction stream 710 and the video stream 720 are packed into an output stream 730, as shown in FIG. 7B. Thus, the output stream 730 can be transmitted to the remote participant of the video conference through the network interface unit 150. Meanwhile, the local participant also receives the output stream from the remote participant, and thus both participants may see each other and share the same interaction data on their respective displays.

Referring to FIG. 5B, in some embodiments, a specific object can be recognized from the captured image. When the specific object has entered the valid zone 520, the specific object will be identified by the processor 120, and the processor 120 may filter out the portion other than the specific object, and then keep rendering the specific object on the display 140. For example, the specific object may be lips of the user. When the user's head approaches the valid zone 520 with a kiss, the lips of the user may first enter the valid zone 520. Thus, the lips of the user will be determined as the specific object, and the processor 120 may keep rendering the lip prints of the user on the display 140.

In an alternative embodiment, the user may hold a specific object (e.g. a doll) on his hand and approach the valid zone 520. When the specific object has entered the valid zone 520, the processor 120 may determine what the specific object being held in the user's hand is using skin color detection techniques, and thus the user's hand can be filtered out from the captured image, and the specific object is left in the captured image. Then, the processor 120 may keep rendering the specific object on the display 140.

In an embodiment, as described in step S240, the processor 120 flips the foreground object horizontally (i.e. reverse left and right). It should be noted that the trajectory of the interaction data from participants in the video conference is shown on the displays of both participants. When the local participant is writing characters from left to right, the remote participant will see that the characters are appearing gradually from left to right on his display. The remote participant may also write additional characters on his display, and thus the interaction data of both users is modified. If the foreground object of the local participant is not flipped horizontally, the remote participant will see that the location on which the local user is writing characters does not match the location where the interaction data is displayed on the display 140, resulting in a poor user experience. Accordingly, the processor 120 flips the foreground object horizontally before performing subsequent image processing, so that both the local participant and the remote participant will see that the location on which the other participant is writing characters matches the location where the interaction data is displayed on the display 140, resulting in a better user experience.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A video conferencing system, comprising:
a display;
an image capturing unit comprising an image sensor to capture images of a local user in a video conference;
a network interface unit, configured to exchange output streams from the local user and a remote user in the video conference; and
a processor, configured to perform foreground segmentation on the captured images to obtain a foreground object, and flip the foreground object horizontally,
wherein the processor further identifies a facing angle, with respecting to the image capturing unit, of a human face from the flipped foreground object and corrects a facing angle of the human face in the flipped foreground object in a manner as if the face is looking toward the image capturing unit,
wherein the processor further determines interaction data from the local user on the display, and encodes the interaction data and the flipped foreground object with the corrected human face into an interaction stream and a video stream, respectively,
wherein the processor further packs the interaction stream and the video stream into the output stream, and transmits the output stream to the remote user through the network interface unit.

2. The video conferencing system as claimed in claim 1, wherein the processor calculates a depth map from the captured images and performs the foreground segmentation according to the depth map.

3. The video conferencing system as claimed in claim 1, wherein the image capturing unit further comprises a depth sensor for detecting depth information of the local user, and the processor builds a depth map according to the depth information and performs the foreground segmentation according to the depth map.

4. The video conferencing system as claimed in claim 1, wherein the processor further calculates image features of the human face of the flipped foreground object, and corrects the facing angle of the human face according to the calculated image features.

5. The video conferencing system as claimed in claim 1, wherein the processor further defines a valid zone in an operating space of the captured images, and when the foreground object has entered the valid zone, the processor records touch points of the foreground object and connects the touch points into lines as a trajectory.

6. The video conferencing system as claimed in claim 5, wherein when the foreground object has entered the valid zone, the processor determines all or a portion of the foreground object as a specific object, and keep rendering the specific object on the display.

7. The video conferencing system as claimed in claim 1, wherein the display is integrated with a touch module, and when a target object of the local user touches a surface of the display, the processor records touch points of the target object and connects the touch points into lines as a trajectory.

8. The video conferencing system as claimed in claim 1, wherein the interaction data is recorded as a binary image, and the processor performs run length encoding on the binary image with Hoffman codes to obtain the interaction stream.

9. The video conferencing system as claimed in claim 1, wherein the processor defines the foreground object as a video object plane, and performs shape coding and texture coding on the foreground object to generate the video stream.

10. The video conferencing system as claimed in claim 1, wherein the display is a transparent display, and the local user sees image of the remote user on the display and background of a local space through the display.

11. A display method for video conferencing, for use in a video conferencing system, wherein the video conferencing system comprises a display, an image capturing unit, and a network interface unit, the method comprising:
utilizing an image sensor of the image capturing unit to capture images of a local user in a video conference;
performing foreground segmentation on the captured images to obtain a foreground object;
flipping the foreground object horizontally;
identifying a facing angle, with respect to the image capturing unit, of a human face from the flipped foreground object and correcting a facing angle of the human face in the flipped foreground object in a manner as if the face is looking toward the image capturing unit;
determining interaction data from the local user on the display;
encoding the interaction data and the flipped foreground object with the corrected human face into an interaction stream and a video stream, respectively;
packing the interaction stream and the video stream into an output stream; and
transmitting the output stream to a remote user of the video conference through the network interface unit.

12. The display method as claimed in claim 11, further comprising:
calculating a depth map from the captured images and performing the foreground segmentation according to the depth map.

13. The display method as claimed in claim 11, wherein the image capturing unit further comprises a depth sensor for detecting depth information of the local user, and the method further comprises:
building a depth map according to the depth information and performing the foreground segmentation according to the depth map.

14. The display method as claimed in claim 11, further comprising:
calculating image features of the human face of the flipped foreground object; and
correcting the facing angle of the human face according to the calculated image features.

15. The display method as claimed in claim 11, further comprising:
defining a valid zone in an operating space of the captured images; and
when the foreground object has entered the valid zone, recording touch points of the foreground object and connecting the touch points into lines as a trajectory.

16. The display method as claimed in claim 15, further comprising:
when the foreground object has entered the valid zone, determining all or a portion of the foreground object as a specific object, and keeping rendering the specific object on the display.

17. The display method as claimed in claim 11, wherein the display is integrated with a touch module, and the method further comprises:
when a target object of the local user touches a surface of the display, recording touch points of the target object and connecting the touch points into lines as a trajectory.

18. The display method as claimed in claim 11, further comprising:
recording the interaction data as a binary image; and
performing run length encoding on the binary image with Hoffman codes to obtain the interaction stream.

19. The display method as claimed in claim 11, further comprising:
defining the foreground object as a video object plane; and
performing shape coding and texture coding on the foreground object to generate the video stream.

20. The display method as claimed in claim 11, wherein the display is a transparent display, and the local user sees image of the remote user on the display and background of a local space through the display.

* * * * *